United States Patent
Raby et al.

(10) Patent No.: US 7,473,097 B2
(45) Date of Patent: Jan. 6, 2009

(54) RFID TRACKING OF PATIENT-SPECIFIC ORTHODONTIC MATERIALS

(75) Inventors: Richard E. Raby, North St. Paul, MN (US); James D. Cleary, Glendora, CA (US); Steven R. Bartingale, Stillwater, MN (US); Russell A. Jordan, Rancho Cucamonga, CA (US)

(73) Assignee: 3M Innovative Properties Company, St. Paul, MN (US)

( * ) Notice: Subject to any disclaimer, the term of this patent is extended or adjusted under 35 U.S.C. 154(b) by 577 days.

(21) Appl. No.: 11/015,368

(22) Filed: Dec. 17, 2004

(65) Prior Publication Data

US 2006/0134580 A1 Jun. 22, 2006

(51) Int. Cl.
*A61C 3/00* (2006.01)
(52) U.S. Cl. .......................... 433/24; 433/213; 433/215
(58) Field of Classification Search ................. 433/24, 433/3, 213, 37–48, 215
See application file for complete search history.

(56) References Cited

U.S. PATENT DOCUMENTS

| | | | |
|---|---|---|---|
| 4,624,640 | A | 11/1986 | Tesini |
| 5,015,180 | A | 5/1991 | Randklev |
| 5,172,809 | A | 12/1992 | Jacobs et al. |
| 5,219,282 | A | 6/1993 | Lavin |
| 5,354,199 | A | 10/1994 | Jacobs et al. |
| 5,429,229 | A | 7/1995 | Chester et al. |
| 5,931,667 | A | 8/1999 | Papandreas |
| 6,059,571 | A | 5/2000 | Kishigami |
| 6,123,544 | A | 9/2000 | Cleary |
| 6,177,870 | B1 | 1/2001 | Lian et al. |
| 6,364,661 | B1 * | 4/2002 | Brattesani .................... 433/37 |
| 6,612,143 | B1 * | 9/2003 | Butscher et al. ............. 72/21.4 |
| 6,731,213 | B1 | 5/2004 | Smith |
| 2002/0017998 | A1 * | 2/2002 | Price ....................... 340/573.1 |
| 2002/0150860 | A1 | 10/2002 | Brattesani |
| 2002/0177108 | A1 | 11/2002 | Pavlovskaia et al. |

(Continued)

FOREIGN PATENT DOCUMENTS

FR 2854055 10/2004

(Continued)

OTHER PUBLICATIONS

Moskowitz et al., "A New Look at Indirect Bonding," Journal of Clinical Orthodontics, vol. XXX, No. 5, pp. 277 et sec., May 1996.

(Continued)

*Primary Examiner*—John J Wilson
(74) *Attorney, Agent, or Firm*—James D. Christoff (57) ABSTRACT

Techniques are described for using radio-frequency identification (RFID) tags to track patient-specific materials throughout the manufacturing of indirect bonding trays. A series of RFID tags may be used to track the patient-specific material starting with the taking of a patient's impression at a clinic within a dental impression tray, through the process of casting and forming the indirect bonding tray at a manufacturing facility, back into the clinic where the appliances are bonded to the patient's teeth, and eventually into storage where the left-over materials may be archived. A database may be used to capture unique identifiers for the RFID tags and other information throughout the process.

21 Claims, 7 Drawing Sheets

U.S. PATENT DOCUMENTS

| | | | |
|---|---|---|---|
| 2003/0002089 A1 | 1/2003 | Vadnais et al. | |
| 2003/0101526 A1 | 6/2003 | Hilscher et al. | |
| 2003/0115694 A1 | 6/2003 | Pace | |
| 2004/0219471 A1 | 11/2004 | Cleary et al. | |
| 2004/0219473 A1 | 11/2004 | Cleary et al. | |
| 2005/0064652 A1 | 3/2005 | Shapira | |
| 2005/0074716 A1 | 4/2005 | Cleary et al. | |
| 2005/0074717 A1 | 4/2005 | Cleary et al. | |
| 2005/0106528 A1* | 5/2005 | Abolfathi et al. | 433/37 |
| 2005/0130095 A1 | 6/2005 | Raby et al. | |
| 2005/0170309 A1 | 8/2005 | Raby et al. | |
| 2005/0233276 A1* | 10/2005 | Kopelman et al. | 433/3 |

FOREIGN PATENT DOCUMENTS

| | | |
|---|---|---|
| WO | WO 88/06869 | 9/1988 |
| WO | WO 02/13719 | 2/2002 |
| WO | WO 2006/023036 | 3/2006 |

OTHER PUBLICATIONS

Raby et al., U.S. Appl. No. 10/903,686, "Automatic Adjustment of an Orthodontic Bracket to a Desired Occlusal Height Within a Three-Dimensional (3D) Enviornment," filed Jul. 20, 2004.

Cinader, Jr. et al., U.S. Appl. No. 11/195,955, "Scanning Models for Digital Orthodontics", filed Aug. 3, 2005.

Cinader, Jr. et al., U.S. Appl. No. 11/195,952, "Registering Physical and Virtual Tooth Structures with Markers", filed Aug. 3, 2005.

Raby et al., U.S. Appl. No. 11/195,954, "Registering Physical and Virtual Tooth Structures with Pedestals", filed Aug. 3, 2005.

Cinader, Jr. et al., U.S. Appl. No. 11/098,317, "Method of Making Indirect Bonding Apparatus for Orthodontic Therapy", filed Apr. 4, 2005.

Cinader, Jr. et al., U.S. Appl. No. 11/128,445, "Method of Making an Indirect Bonding Tray for Orthodontic Treatment", filed May 13, 2005.

"Inside Contactless Chosen To Track Dental Prosthesis," Wednesday, Mar. 31, 2004, http://www.contactlessnews.com/news/2004/03/31/inside-contactless-chosen-to-track-dental-prosthesis/.

"RFID Chip Helps Prevent Surgical Mixups," TechScope Electronics Technology at Work and at Play, dated Dec. 8, 2004, www.elecdesign.com.

* cited by examiner

RFID TRACKING OF PATIENT-SPECIFIC ORTHODONTIC MATERIALS

TECHNICAL FIELD

The invention relates to orthodontics and, more particularly, techniques for tracking orthodontic materials.

BACKGROUND

The field of orthodontics is concerned with repositioning and aligning a patient's teeth for improved occlusion and aesthetic appearance. For example, orthodontic treatment often involves the use of tiny slotted appliances, known as brackets, that are fixed to the patient's anterior, cuspid, and bicuspid teeth. An archwire is received in the slot of each bracket and serves as a track to guide movement of the teeth to desired orientations. The ends of the archwire are usually received in appliances known as buccal tubes that are secured to the patient's molar teeth.

A number of orthodontic appliances in commercial use today are constructed on the principle of the "straight wire concept" developed by Dr. Lawrence F. Andrews, D.D.S. In accordance with this concept, the shape of the appliances, including the orientation of the slots of the appliances, is selected so that the slots are aligned in a flat reference plane at the conclusion of treatment. Additionally, a resilient archwire is selected with an overall curved shape that normally lies in a flat reference plane.

When the archwire is placed in the slots of the straight wire appliances at the beginning of orthodontic treatment, the archwire is often deflected upwardly or downwardly from one appliance to the next in accordance with the patient's malocclusions. However, the resiliency of the archwire tends to return the archwire to its normally curved shape that lies in a flat reference plane. As the archwire shifts toward the flat reference plane, the attached teeth are moved in a corresponding fashion toward an aligned, aesthetically pleasing array.

In general, orthodontic appliances that are adapted to be adhesively bonded to the patient's teeth are placed on the teeth by either one of two methods: a direct bonding method, or an indirect bonding method. In the direct bonding method, the appliance and adhesive are grasped with a pair of tweezers or other hand instrument and placed by the practitioner on the surface of the tooth in an approximate desired location. Next, the appliance is shifted along the surface of the tooth as needed until the practitioner is satisfied with its position. Once the appliance is in its precise, intended location, the appliance is pressed firmly onto the tooth to seat the appliance in the adhesive. Excess adhesive in areas adjacent the base of the appliance is removed, and the adhesive is then allowed to cure and fix the appliance firmly in place. Typical adhesives include light-curable adhesives that begin to harden upon exposure to actinic radiation, and two-component chemical-cure adhesives that begin to harden when the components are mixed together.

While the direct bonding technique described above is in widespread use and is considered satisfactory by many, there are shortcomings that are inherent with such a technique. For example, access to surfaces of malposed teeth may be difficult. In some instances, and particularly in connection with posterior teeth, the practitioner may have difficulty seeing the precise position of the bracket relative to the tooth surface. Additionally, the appliance may be unintentionally bumped from its intended location during the time that the excess adhesive is being removed adjacent the base of the appliance.

Another problem associated with the direct bonding technique described above concerns the significant length of time needed to carry out the procedure of bonding each appliance to each individual tooth. Typically, the practitioner will attempt to ensure that each appliance is positioned in its precise, intended location before the adhesive is cured, and some time may be necessary before the practitioner is satisfied with the location of each appliance. At the same time, however, the patient may experience discomfort and have difficulty in remaining relatively motionless, especially if the patient is an adolescent. As can be appreciated, there are aspects of the direct bonding technique that can be considered a nuisance for both the practitioner and for the patient.

Indirect bonding techniques often avoid many of the problems noted above. In general, indirect bonding techniques known in the past have involved the use of a transfer tray having a shape that matches the configuration of at least part of a patient's dental arch. A set of appliances such as brackets are releasably connected to the tray at certain, predetermined locations. Adhesive is applied to the base of each appliance, and the tray is then placed over the patient's teeth until such time as the adhesive hardens. Next, the tray is detached from the teeth as well as from the appliances, with the result that all of the appliances previously connected to the tray are now bonded to the respective teeth at their intended, predetermined locations.

In more detail, one method of indirect bonding of orthodontic appliances includes the steps of taking an impression of each of the patient's dental arches and then making a replica plaster or "stone" model from each impression. Optionally, a soap solution (such as Model Glow brand solution from Whip Mix Corporation) or wax is applied to the stone model. A separation solution (such as COE-SEP brand tinfoil substitute from GC America, Inc.) is then applied to the stone model and allowed to dry. If desired, the teeth of the model can be marked with a pencil to assist in placing the brackets in ideal positions.

Next, the brackets are bonded to the stone models. Optionally, the bonding adhesive can be a chemical curing adhesive (such as Concise brand adhesive from 3M) or a light-curable adhesive (such as Transbond XT brand adhesive or Transbond LR brand adhesive, from 3M). Optionally, the brackets may be adhesive precoated brackets such as those described in. U.S. Pat. Nos. 5,015,180, 5,172,809, 5,354,199 and 5,429, 299.

A transfer tray is then made by placing a matrix material over the model as well as over the brackets placed on the model. For example, a plastic sheet matrix material may be held by a frame and exposed to radiant heat. Once the plastic sheet material has softened, it is placed over the model and the brackets. Air in the space between the sheet material and the model is then evacuated, and the plastic sheet material assumes a configuration that precisely matches the shape of the replica teeth of the stone model and the attached brackets.

The plastic material is then allowed to cool and harden to form a tray. The tray and the brackets (which are embedded in an interior wall of the tray) are then detached from the stone model and sides of the tray are trimmed as may be desired. Once the patient has returned to the office, a quantity of adhesive is placed on the base of the bracket, and the tray with the embedded brackets is then placed over the matching portions of the patient's dental arch. Since the configuration of the interior of the tray closely matches the respective portions of the patient's dental arch, each bracket is ultimately positioned on the patient's teeth at precisely the same location that corresponds to the previous location of the same bracket on the stone model.

Both light-curable adhesives and chemical curing adhesives have been used in the past in indirect bonding techniques to secure the brackets to the patient's teeth. If a light-curable adhesive is used, the tray is preferably transparent or translucent. If a two-component chemical curing adhesive is used, the components can be mixed together immediately before application of the adhesive to the brackets. Alternatively, one component may be placed on each bracket base and the other component may be placed on the tooth surface. In either case, placing of the tray with the embedded brackets on corresponding portions of the patient's dental arch enables the brackets to be bonded to the teeth as a group using only a short amount of time that the patient is occupying the chair in the operatory. With such a technique, individual placement and positioning of each bracket in seriatim fashion on the teeth is avoided.

A variety of transfer trays and materials for transfer trays have been proposed in the past. For example, some practitioners use a soft sheet material (such as Bioplast tray material from Scheu-Dental GmbH or Great Lakes Orthodontics, Ltd.) for placement over the stone model and the appliances on the model. Either a vacuum or positive pressure is applied to respectively pull or push the soft material into intimate contact with the model and the appliances on the model. Next, a stiffer sheet material (such as Biocryl sheet material, from Scheu-Dental GmbH or Great Lakes Orthodontics, Ltd.) is formed over the softer sheet material, again using a either a vacuum or positive pressure forming technique. The stiffer material provides a backbone to the tray, while the softer material initially holds the appliances and yet is sufficiently flexible to release from the appliances after the appliances have been fixed to the patient's teeth.

It has also been proposed in the past to use a silicone impression material or a bite registration material (such as Memosil 2, from Heraeus-Kulzer GmbH-& Co. KG). The silicone material is applied over the appliances that are attached to the study model so that the appliances are partially encapsulated.

In an article entitled "A New Look at Indirect Bonding" by Moskowitz et al. (Journal of Clinical Orthodontics, Volume XXX, Number 5, May 1996, pages 277 et sec.), a technique for making indirect bonding trays is described using Reprosil impression material (from Dentsply International). The impression material is placed with a syringe over brackets that have been previously placed on a stone model. Next, a sheet of clear thermoplastic material is drawn down over the impression material using a vacuum-forming technique. The resultant transfer tray is then removed from the model for subsequent placement on the patient's dental arch.

Indirect bonding techniques offer a number of advantages over direct bonding techniques. For one thing, and as indicated above, it is possible to bond a plurality of brackets to a patient's dental arch simultaneously, thereby avoiding the need to bond each appliance in individual fashion. In addition, the indirect bonding tray helps to locate all of the brackets in their proper, intended positions such that adjustment of each bracket on the surface of the tooth before bonding is avoided. The increased placement accuracy of the appliances that is often afforded by indirect bonding techniques helps ensure that the patient's teeth are moved to their proper, intended positions at the conclusion of treatment.

Proper handling of patient-specific materials is potentially one of the most important aspects of an orthodontic indirect bonding process. Each indirect bonding tray that is manufactured is based on either a standard prescription or a customized, patient-specific prescription. In either case, the prescription defines a discrete set of orthodontic brackets or other appliances that is to be incorporated into the indirect bonding tray that is manufactured for the particular patient. It is vital that the manufacturer use the prescribed set of brackets, and that each bracket is correctly associated with its respective tooth. Errors in the prescription can result in failures ranging from delays in processing and delivery to damaged manufacturing equipment to lost customer confidence and even harm to the patient. It is, therefore, important to properly identify each physical impression, model, indirect bonding tray and appliance. Similarly, these physical objects must be properly associated with the patient to which they correspond, the doctor who ordered the components and the clinic in which the doctor practices.

SUMMARY

In general, the invention relates to techniques for using radio-frequency identification (RFID) tags to track patient-specific materials throughout the manufacturing of indirect bonding trays. A series of RFID tags may be used to track the patient-specific material starting with the taking of a patient's impression at a clinic within a dental impression tray, through the process of casting and forming the indirect bonding tray at a manufacturing facility, back into the clinic where the appliances are bonded to the patient's teeth, and eventually into storage where the left-over materials may be archived. A database may be used to capture unique identifiers for the RFID tags and other information throughout the process.

Techniques are employed to ensure that the proper correct materials are associated with the patient, such as preferably transferring digital information between the RFID tags only when their associated materials are physically coupled. For example, digital information may be transferred from an RFID tag associated with the dental impression tray to a model of the impression while the model is being formed from the impression. Similarly, digital information may be transferred from the RFID tag of the model to an RFID tag embedded within or otherwise affixed to the indirect bonding tray while the indirect bonding tray is being formed from the model.

In one embodiment, a method comprises forming a casting from a dental impression tray having an impression of a tooth structure of a patient, wherein the dental impression tray includes a radio-frequency identification (RFID) tag. The method further comprises associating an RFID tag with the casting, and storing digital information that associates the RFID tag of the casting with the RFID tag of the dental impression tray.

In another embodiment, a system comprises a model of a tooth structure of a patient, and an indirect bonding tray physically coupled to the model. The model includes at least one orthodontic appliance and an RFID tag storing digital information. An RFID system associates the digital information from the RFID tag of the model with digital information from the RFID tag of the indirect bonding tray.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
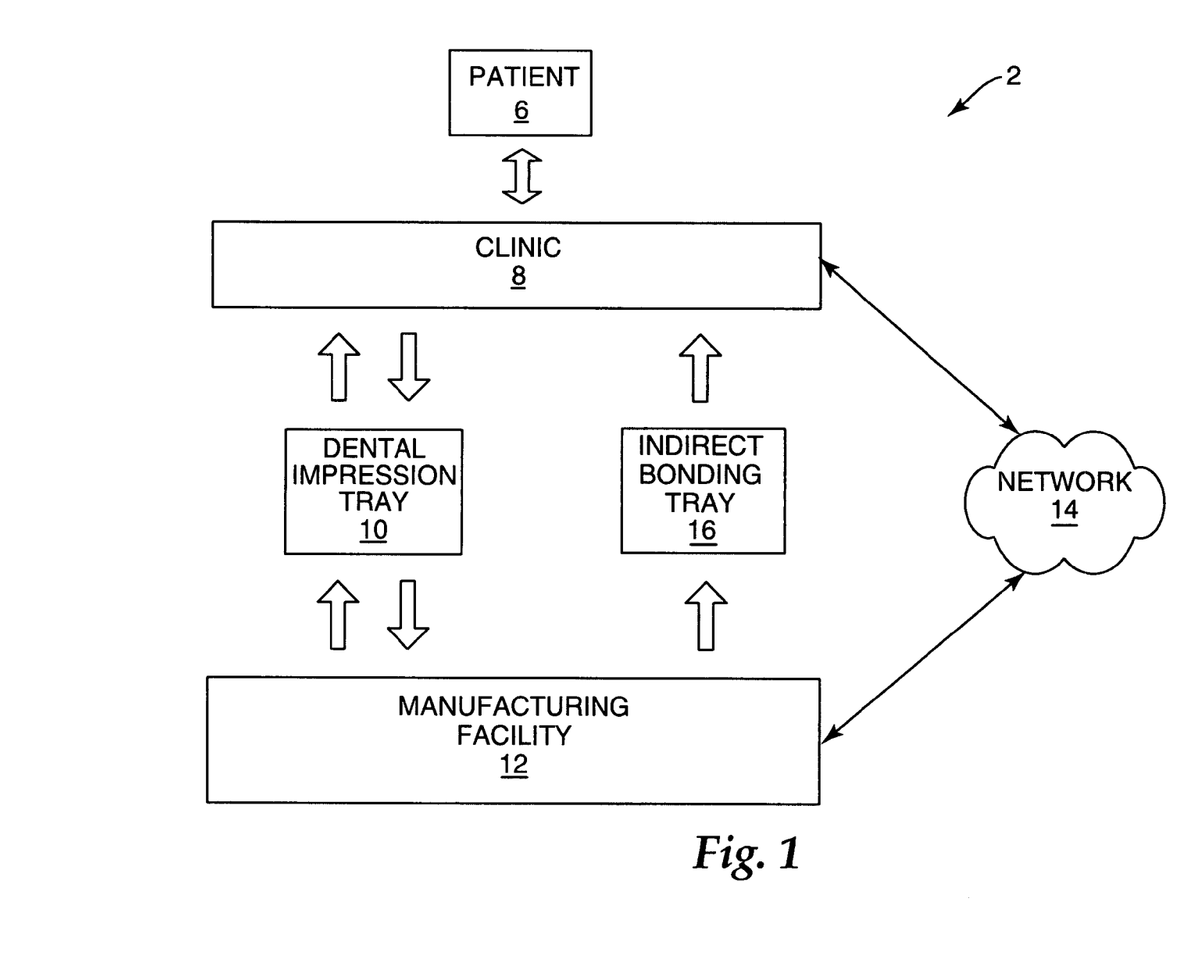
FIG. 1 is a block diagram illustrating an exemplary computer environment in which radio-frequency identification (RFID) techniques are utilized to track patient-specific materials throughout an indirect bonding tray manufacturing process.

FIG. 1 is a block diagram illustrating an exemplary computer environment in which radio-frequency identification (RFID) techniques are utilized to track patient-specific materials throughout an indirect bonding tray manufacturing process. Initially, manufacturing facility 12 produces a dental impression tray 10 for receiving dental impressions of a dental arch or other tooth structure of patient 6. During manufacturing, the manufacturing facility 12 inserts an RFID tag within, or otherwise affixes the RFID tag to, dental impression tray 10 to ensure that the dental impression tray is capable of receiving and/or storing digital information. Manufacturing facility 12 ships dental impression tray 10 to clinic 8. The dental impression tray 10 is preloaded with a quantity of impression material by the manufacturer before shipment to the practitioner, or alternatively is loaded with a quantity of impression material once the tray 10 arrives in clinic 8.

An orthodontic practitioner of clinic 8 utilizes dental impression tray 10 to capture an impression of the dental arch of patient 6. Before, during or after this process, clinic 8 either programs the RFID tag of dental impression tray 10 with digital information identifying patient 6 or copies the read-only digital information already stored in the tag to a patient record in a database, depending on which type of tag is used. For example, one or more RFID stations may be placed within a records room or other location within clinic 8 at or near the location where the impressions are made. Other information may be stored within the RFID tag, such as data identifying clinic 8, a date and time the impression was captured and other information that may be useful throughout the manufacturing process. It may be preferable to program the RFID tag of dental impression tray 10 as near as possible to the actual time the impression is made to reduce any possibility that the dental impression tray 10 is associated with the incorrect patient.

In addition to, or instead of, programming the RFID tag of dental impression tray 10, clinic 8 stores digital information in a patient record within a database to associate the patient record with the particular dental impression tray 10. Clinic 8 may, for example, update a local database having a plurality of patient records. Alternatively, clinic 8 may remotely update a central database within manufacturing facility 12 via network 14. In some embodiments, the database associates the patient record with a unique identifier within the RFID tag of dental impression tray 10, thereby logically associating dental impression tray 10 with patient 6 without storing the patient identifier within its corresponding RFID tag. This technique may provide additional privacy and security for the patient information. Further, this technique may allow read-only RFID tags to be utilized throughout the manufacturing process without worry of data loss or corruption.

In either case, clinic 8 then returns dental impression tray 10 to manufacturing facility 12. Manufacturing facility 12 utilizes dental impression tray 10 to construct an indirect bonding tray 16 for use in physically placing brackets on the teeth of patient 6. Manufacturing facility 12 may, for example, use conventional commercially-available brackets selected by clinic 8 to form indirect bonding tray 16. Suitable indirect bonding trays and methods for making indirect bonding trays are described, for example, in copending and commonly assigned U.S. Pat. No. 7,020,963 entitled "Method and Apparatus for Indirect Bonding of Orthodontic Appliances", filed May 2, 2003 to Cleary et al., U.S. Pat. No. 7,188,421 entitled "Orthodontic Appliances Having a Contoured Bonding Surface", filed May 2, 2003 to Cleary et al., and Ser. No. 10/678,841 entitled "Method and Apparatus for Bonding Orthodontic Appliances to Teeth", filed Oct. 3, 2003 to Cleary et al., all of which are entirely incorporated herein by reference. Manufacturing facility 12 forwards indirect bonding tray 16 to clinic 8 for use in a conventional indirect bonding procedure to place the brackets on the teeth of patient 6.

As described in further detail below, manufacturing facility 12 may utilize additional RFID tags to ensure proper tracking of patient-specific materials during the manufacturing process. For example, manufacturing facility 12 may embed an RFID tag within a casting (i.e., physical model) made from dental impression tray 10. Manufacturing facility 12 then stores digital information that associates the RFID tag of dental impression tray 10 with the RFID tag of the casting. For example, manufacturing facility 12 may update the database to store unique identifiers from the RFID tags. As another example, manufacturing facility may transfer at least some of the digital information stored within the RFID tag of dental impression tray 10 to the RFID tag within the casting. In some embodiments, manufacturing facility 12 may read the digital information from the RFID tag of dental impression tray 10 and program the RFID tag within the casting while the casting is physically coupled to the dental impression. In this manner, manufacturing facility 12 ensures that the digital information is transferred from dental impression tray 10 to the corresponding casting.

Manufacturing facility 12 utilizes the RFID tag within the casting to track the casting throughout the manufacturing process after separation from dental impression tray 10. For example, manufacturing facility 12 may utilize RFID readers to read and program the RFID tag as the casting travels to a curing oven, a trimming station, a pedestal bonding station and a robotic appliance placement station. At every station, manufacturing facility 12 reads the RFID tag of the casting to update a status and record timestamps within the RFID tag itself, the database or both.

Further, manufacturing facility 12 may use additional RFID tags at the robotic appliance placement station to ensure proper selection of prescribed appliances. For example, as further described below, RFID tags may be fixed to magazines of orthodontic appliances (e.g., brackets) and used to verify that the types of bracket being placed on the casting match the prescription selected for the patient to which the casting corresponds. In this manner, manufacturing facility 12 utilizes the digital information in the RFID tag of the casting or the database to confirm that the correct brackets are selected and placed on the casting.

Manufacturing facility 12 then forms indirect bonding tray 16 from the casting and the brackets affixed to the casting. For example, manufacturing facility 12 may produce indirect bonding tray 16 by placing a matrix material in the form of a plastic sheet over the casting and the brackets and exposing the matrix material to radiant heat. Air in the space between the sheet material and the model is then forced out by a pressure differential between the inner and outer surfaces of the sheet material (i.e., either by vacuum forming or positive pressure forming), and the plastic sheet material assumes a configuration that precisely matches the shape of the replica teeth of the stone model and the attached brackets.

The manufacturing facility then connects an RFID tag to the indirect bonding tray 16. As one example, before the matrix material of indirect bonding tray 16 is allowed to completely cool or otherwise cure, manufacturing facility 12 may at least partially embed the RFID tag within the matrix material. As another example, the manufacturing facility connects the RFID tag to the matrix material by an adhesive, or captures the RFID tag between two layers of matrix material (in the latter example, the outer layer of matrix material may comprise a relatively hard outer tray or shell and the inner layer of matrix material may comprise a relatively flexible material, as described in the aforementioned U.S. Patent Application Publication No. 04-0219471-A1. Manufacturing facility 12 then stores digital information that associates the RFID tag of the casting with the RFID tag of indirect bonding tray 16. For example, manufacturing facility 12 may update the database to stare unique identifiers from the RFID tags. As another example, manufacturing facility may transfer the digital information stored within the RFID tag of the casting to the RFID tag within indirect bonding tray 16. Manufacturing facility 12 may also update the digital information to include a timestamp of when indirect bonding tray 16 was formed and other information, such as the identification information for manufacturing facility 12 and any personnel involved in the manufacture of the indirect bonding tray. In this manner, the RFID tag of indirect bonding tray 16 may store a variety of digital information including the digital information originally programmed in the RFID tag of impression model 10 and transferred to the RFID tag of the casting.

In some embodiments, manufacturing facility 12 may read the digital information from the RFID tag of the casting and update the database or program the RFID tag of indirect bonding tray 16 while the indirect bonding tray is still physically coupled to the casting. In this manner, manufacturing facility 12 ensures that the digital information is properly transferred from the casting to the corresponding indirect bonding tray 16 for patient 6.

The matrix material is then allowed to cool and harden, or otherwise cure and harden, to form indirect bonding tray 16. Indirect bonding tray 16 and the brackets are then detached from the casting, and manufacturing facility 12 ships the indirect bonding tray to clinic 8. The RFID tag within the indirect bonding tray 16 may be used to record a shipment date and time, which may be made available to clinic 8 via network 14.

Clinic 8 may utilize the RFID tag within indirect bonding tray 16 to record a date and time of receipt. Moreover, clinic 8 interrogates the RFID tag with an RFID reader to ensure that indirect bonding fray 16 is applied to the proper patient i.e., patient 6 in this example. In particular, once patient 6 has returned to clinic 8, clinic 8 interroagates indirect bonding tray 16 to confirm that the digital information contained within the RFID tag matches the database record for patient 6. If so, the orthodontic practitioner proceeds with the indirect bonding process by placing a quantity of adhesive on the base of each bracket, and then placing the fray with the embedded brackets over the matching portions of the patient's dental arch. Alternatively, a quantity of bonding adhesive may be pro-applied to base of the brackets by the manufacturer, as described in copending and commonly assigned U.S. Patent Application Publication No. 05-0074716-A1, Apr. 7, 2005 entitled "Apparatus for Indirect Bonding of Orthodontic Appliances and Method of Making the Same", to Cleary et al. Since the configuration of the interior of indirect bonding tray 16 closely matches the respective portions of the dental arch of patient 6, each bracket is ultimately positioned on the patient's teeth at precisely the same location that corresponds to the previous location of the same bracket on the casting used to produce the indirect bonding tray. Once the adhesive is cured, the practitioner then detaches indirect bonding tray 16, and the brackets remain affixed to the dental arch of the patient 6.

Indirect bonding tray 16 may then be stored within clinic 8, manufacturing facility 12 or elsewhere for the duration of the treatment period so that the tray may be used subsequently to re-bond one or more brackets in case of bond failure. The RFID tag embedded in indirect bonding tray 16 may allow a practitioner to retrieve the tray from storage with confidence that the correct tray is being used once again. At the conclusion of treatment, the trays may either be discarded or archived for study or legal purposes.

In this manner, RFID techniques are utilized to track patient-specific materials throughout an indirect bonding tray manufacturing process. The techniques may be used to ensure proper association between patient 6 and the patient-specific material. The techniques may be used to store digital information (e.g., unique tag identifiers) within a database to associate patient-specific materials and/or to transfer digital information through a series of RFID tags through the process, i.e., from initial formation of the impressions to ultimate application of indirect bonding tray 16.

Figure 2:
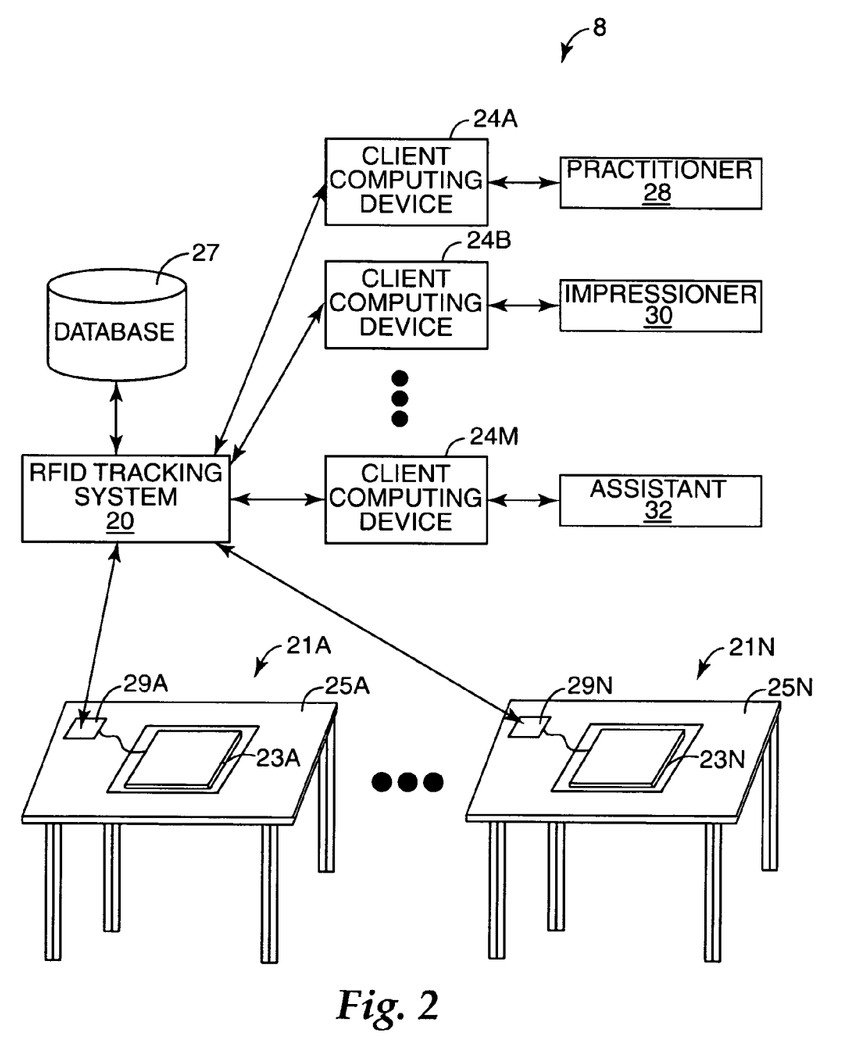
FIG. 2 is a block diagram illustrating a simplified view of a computer environment within an orthodontic clinic.

FIG. 2 is a block diagram illustrating a simplified view of clinic 8. In this example, clinic 8 includes an RFID tracking system 20 that is used to track dental impression trays, indirect bonding trays, such as dental impression tray 10 and indirect bonding tray 16 of FIG. 1. Additionally, clinic 8 may utilize RFID tracking system 20 to track other articles, such as patient files, billing records or other articles.

As described, clinic 8 utilizes RFID tags that uniquely identify the articles, e.g., by unique serial numbers associated with the tags. In addition, RFID tracking system 20 may write additional information to the RFID tags, such as identification information for the particular patient with which the article (e.g., dental impression tray or indirect bonding tray) is associated, status information indicating whether article has been used, one or more timestamps, identification information for clinic 8 and other information. Optionally, if the RFID tags have sufficient storage capability, the tags may include prescription information such as the identity and position of the brackets relative to the patient's teeth, along with data representing the shape of the patient's dental arch.

In general, RFID tracking system 20 operates within a defined frequency range of the electromagnetic spectrum, such as 13.56 MHz, with an allowable frequency variance of +/−7 kHz. However, other frequencies may be used for RFID applications. For example, some RFID systems operate at approximately 900-928 MHz.

The RFID tags themselves may take any number of forms without departing from the scope of the present invention. Examples of commercially available RFID tags include 3M™ RFID tags available from 3M Company, St. Paul, Minn., or "Tag-it" RFID transponders available from Texas Instruments, Dallas, Tex. An RFID tag typically includes an integrated circuit operatively connected to an antenna that receives RF energy from a source and backscatters RF energy in a manner well known in the art. The backscattered RF energy provides a signal that the RFID tag modulates to communicate information about the RFID tag and its associated article.

RFID tracking system 20 may provide or otherwise communicate with a database 27 to store the tag information for each indirect bonding tray or other article used by clinic 8. Database 27 may be located within clinic 8 and optionally configured to share data with a database within manufacturing facility 12. Alternatively, database 27 may be located within manufacturing facility 12 and remotely accessible via clinic 8. RFID tracking system 20 may be networked or otherwise coupled to one or more client computing devices 24A-24M so that individuals at various RFID stations 21A-21N can program the tags and/or access data relative to those items. RFID stations 21 typically include RFID readers 29A-29N coupled to antennas 23A-23N for interrogating the RFID tags fixed to articles and programming the RFID tags as desired. Although not illustrated, clinic 8 may use other RFID readers, such as handheld RFID readers, intelligent storage locations having built-in RFID readers and the like.

An assistant 32 may record receipt of dental impression tray 10 and indirect bonding tray 16 from manufacturing facility 12 by placing the articles on or near an RFID station, e.g., RFID station 21A, and interacting with client computing device 24M. In particular, upon sensing and interrogating the RFID tags embedded within dental impression tray 10 and indirect bonding tray 16, RFID tracking system 20 may record the unique identifiers for the RFID tags within database 27. RFID tracking system 20 may then access the RFID tags to record a date and time of receipt and set an initial (unused) status of the RFID tags until an impression is taken. Alternatively, or in addition to, the RFID tracking system may store the date and time of receipt, along with an initial status in database 27.

As another example, after making an impression of a dental arch of patient 6, impressioner 30 may place dental impression tray 10 on or near one of RFID stations 21 to associate the dental impression tray with the patient before, during or after capture of an impression of the dental arch of the patient.

Further, at some later point, practitioner 28 may place indirect bonding tray 16 on or near one of RFID stations 21 prior to transferring the brackets to the dental arch of patient 6 to confirm that the correct indirect bonding tray is being used.

In one embodiment, practitioner 28 may interact with client computing device 24A to select or define a prescription for use by manufacturing facility 12 to produce indirect bonding tray 16. For example, client computing device 24A may present a user interface by which practitioner 28 defines a prescription, i.e., selects one or more brackets and associates each bracket with a particular tooth of the dental arch of patient 6. In one embodiment, client computing device 24A is a modeling workstation that provides an environment for presenting a three-dimensional (3D) representation of a dental arch of patient 6. Orthodontic practitioner 28 interacts with modeling software executing on client computer device 24A to visualize the 3D representation of the dental arch, and precisely position "virtual" brackets on individual teeth within the modeled dental arch.

The 3D representation of the dental arch may be generated by digitally scanning dental impression tray 10 (or a physical model of the teeth made from the dental impression tray) after capturing an impression of the teeth of patient 6. Dental impression tray 10 may be scanned, for example, at clinic 8 or manufacturing facility 12. Alternatively, practitioner 28 may use an intraoral scanner to produce the 3D digital representation directly from the teeth of patient 6.

Practitioner 28 interacts with the modeling software to view the 3D digital representation of the teeth and select the point on each tooth where the respective bracket is to be located. During this process, the modeling software manipulates each bracket as a separate object within the 3D environment, and fixes the position of each bracket within the 3D space relative to a coordinate system associated with the bracket's respective tooth. Consequently, practitioner 28 is able to independently view and precisely locate each bracket within the 3D environment relative to its respective tooth.

Once practitioner 28 has placed the brackets and indicated his or her approval, client computing device 24A communicates the bracket placement positions to manufacturing facility 12 via network 14 (FIG. 1). Manufacturing facility 12 utilizes the bracket placement positions when manufacturing indirect bonding tray 16 and, more particularly, when robotically placing brackets on the casting formed from dental impression tray 10. Alternatively, client computing device 24A need not forward the bracket placement positions to manufacturing facility 12. Client computing device 24A may instead output, e.g., display or print, the relevant distances and angles for each bracket to assist practitioner 28 in manually positioning the brackets on the teeth of patient 6. Moreover, clinic 8 and manufacturing facility 12 may utilize the RFID techniques described to track patient-specific material regardless of whether the clinic utilizes the 3D modeling environment to select bracket placement positions. Clinic 8 and manufacturing facility 12 may share the same location, as might be the case for a clinic with an extensive in-office laboratory where indirect bonding trays are manufactured. In this case, certain steps in the process, such as shipping and receiving, would not apply.

In some embodiments, RFID tracking system 20 may take the form of an RFID inventory management system to manage inventory of incoming dental impressions, models, indirect bonding trays, patient-specific documents and other articles. Clinic 8 may include "smart" storage areas (e.g., shelves, vertical files, carts, bins, cabinets, boxes or other locations) that are RFID-enabled. The smart storage areas may be equipped with one or more antennas for interrogating RFID tags to aid in determining which articles are located at each of the storage areas. The antennas may be positioned in various ways, such as on top or bottom of a storage area, at the back of a storage area, or supported vertically, interspersed among the articles. The antennas can be retrofitted to existing storage areas or built into a storage area and purchased as a unit.

The information collected by RFID tracking system 20 may be useful in locating articles as well as tracking, for example, cycle time and efficiency of one or more people who work with the articles. One example of an RFID tracking system incorporating "smart" storage areas and an exemplary RFID antenna for use in such a system is described in commonly assigned U.S. Pat. No. 6,861,993, issued Mar. 1, 2005, entitled "MULTI-LOOP ANTENNA FOR RADIO-FREQUENCY IDENTIFICATION", to Michele A Waldner, hereby incoporated by reference.

Figure 3:
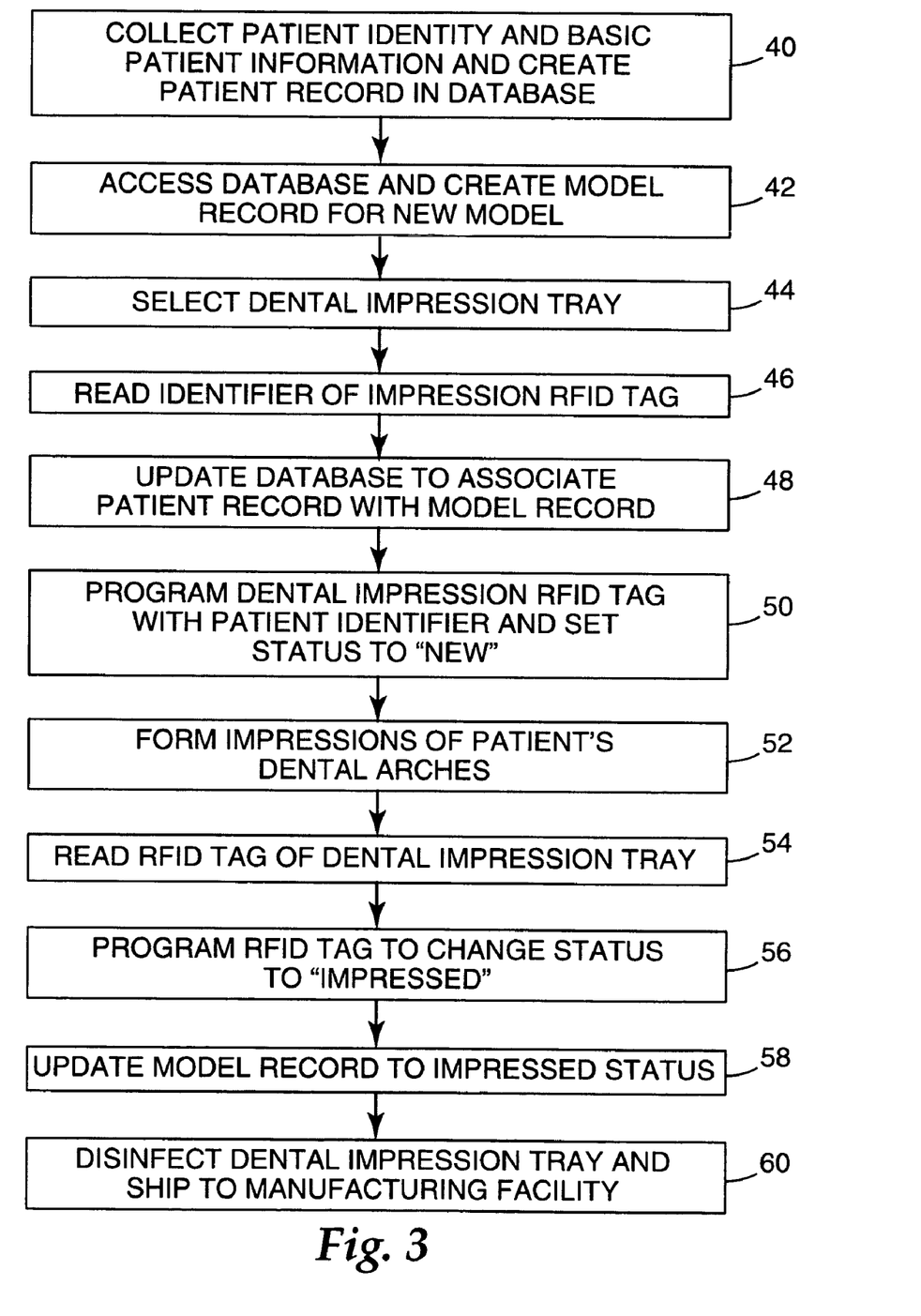
FIG. 3 is a flowchart illustrating an exemplary process performed by a clinic in utilizing the RFID techniques described herein.

FIG. 3 is a flowchart illustrating an exemplary process performed by clinic 8 in utilizing the RFID techniques described herein. Initially, assistant 32 collects patient identity and other information from patient 6 and creates a patient record within database 27 (40). As described, database 27 may be located within clinic 8 and optionally configured to share data with a database within manufacturing facility 12. Alternatively, database 27 may be located within manufacturing facility 12 and remotely accessible via clinic 8.

When capturing an impression of the dental arch of patient 6, or shortly before or after, impressioner 30 interacts with database 27 via client computer 24B to create a model record for a new dental impression (42). Impressioner 30 then selects a new dental impression tray 10 (44), and places the selected dental impression tray within the electromagnetic field of one of RFID stations 21 in order to read the unique identifier of the RFID tag embedded within the dental impression tray (46).

Impressioner 30 then directs the client computer, such as client computer 24B, to update database 27 to store the unique identifier within the model record, and associate the model record with the patient record for patient 6 (48). For example, database 27 may update a foreign key within a relational table to logically link the newly created model record and the patient record for patient 6. Client computer 24B may read patient information, such as a patient identifier, and automatically direct the RFID station to program the RFID tag within dental impression tray 10 to digitally record the patient information from the patient record of database 27 (50). Client computer 24B may also direct the RFID station to change a status within the RFID tag to a "NEW" or "INITIALIZED" status to indicate that dental impression tray 10 has not yet been utilized to capture a dental impression of patient 6.

Impressioner 30 then utilizes the dental impression tray 10 to capture an impression of the dental arch of patient 6 (52). After capturing the dental impression, impressioner 30 removes dental impression tray 10 from the mouth of the patient and places the dental impression tray on or near an RFID station 21. The RFID station 21 again reads the tag identifier from the RFID tag of dental impression tray 10 (54), and programs the RFID tag to change the status to "IMPRESSED" (56). The RFID station 21 may also program the RFID tag to store data identifying clinic 8, a date and time the impression was captured, an identification of impressioner 30, an identifier of the requesting practitioner and other information that may be useful throughout the manufacturing process.

Client computer 24B similarly updates the database model record for dental impression tray 10 to reflect the "IMPRESSED" status as well as store any of the information that may additionally be written to the RFID tag (58). Impressioner 30 then removes dental impression tray from the RFID station 21 and deposits the dental impression tray in a sterilization bath (60). Due to the unique information maintained with the embedded RFID tag, dental impression tray 10 may be disinfected, dried and shipped to manufacturing facility 12 either individually or in batch. During the shipment process, the RFID tag within dental impression tray 10 may be used to assign and record a shipment date and time within the RFID tag, the database or both. The status within the RFID tag may also be changed to a "SHIPPED" status.

Figure 4A:
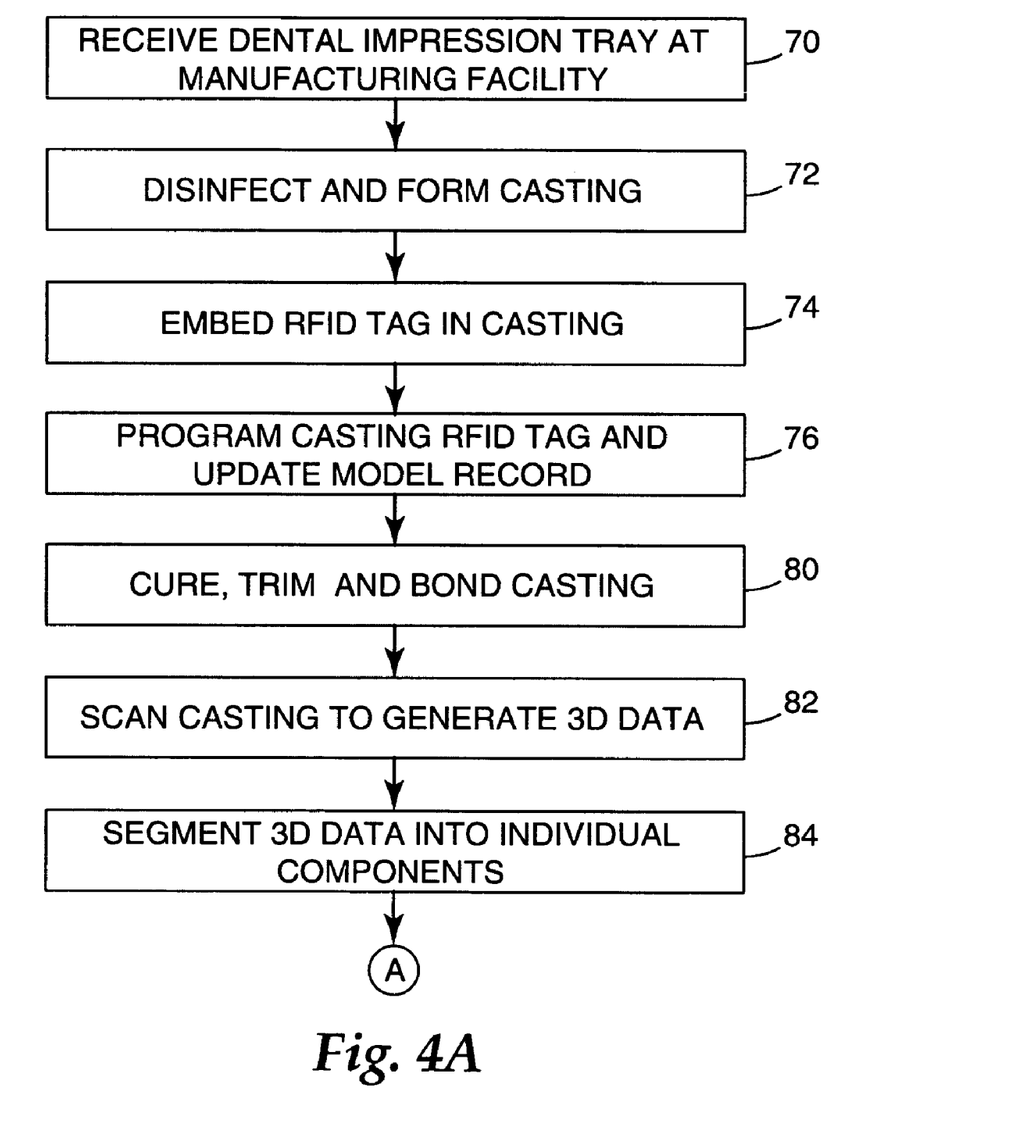
FIGS. 4A and 4B are a flowchart illustrating a process performed by a manufacturing facility in utilizing the RFID techniques described herein.
Figure 4B:
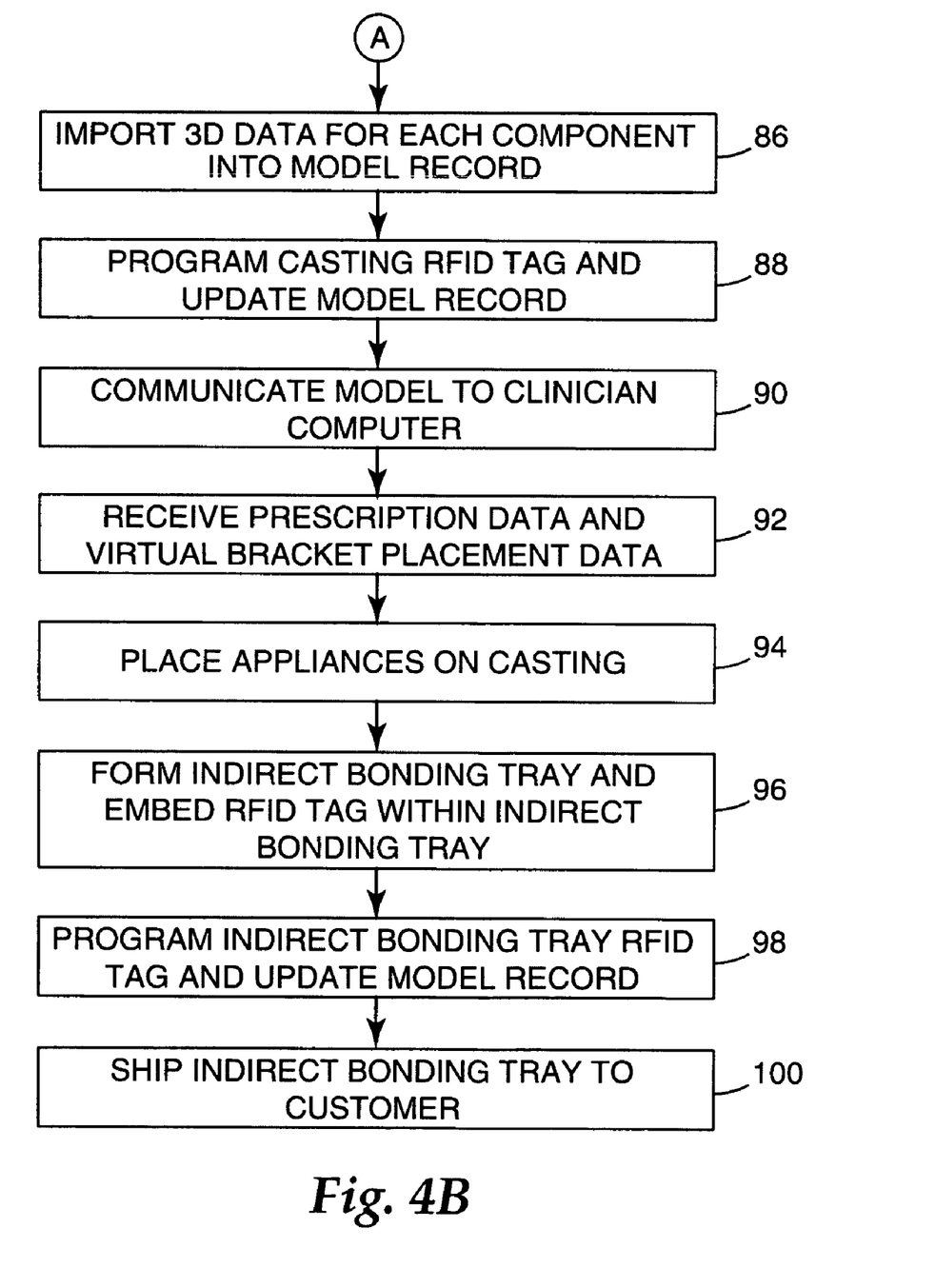

FIGS. 4A and 4B are a flowchart illustrating a process performed by manufacturing facility 12. Manufacturing facility 12 typically receives dental impression tray 10 as part of a larger shipment containing multiple dental impressions. Personnel within manufacturing facility 12 processes the shipment with an RFID station to read the digital information from the RFID tag embedded within dental impression tray 10 (70). The RFID station located in the receiving area updates a database, e.g., a central database maintained within manufacturing facility 12, to update the model record to indicate receipt of dental impression tray 10 and specify the date and time of receipt. Clinic 8 may access this information via network 14 to verify that the impressions were not lost during shipment.

Next, manufacturing facility 12 sterilizes the shipment of impression trays, including dental impression tray 10, and moves the dental impression trays to a casting station where castings are made from the trays (72). The term "casting" is used generally herein to refer to any type of physical model made from dental impression tray 10. For example, a replica plaster or "stone" model from each impression.

During this process, manufacturing facility 12 embeds an RFID tag within the casting material (e.g., epoxy or plaster) before the material solidifies (74). Once the casting sets, manufacturing facility 12 stores digital information that associates the RFID tag of the casting with the RFID tag of dental impression tray 10. For example, manufacturing facility 12 may update the database to store unique identifiers from the RFID tags. As another example, manufacturing facility may transfer the digital information stored within the RFID tag of dental impression tray 10 to the RFID tag within the casting (76). Manufacturing facility 12 utilizes an RFID station located at or near the casting station to read the digital information from the RFID tag of dental impression tray 10 and optionally program the RFID tag within the casting while the casting is physically coupled to the dental impression tray. In this manner, manufacturing facility 12 ensures that the digital information from dental impression tray 10 is associated with the correct (i.e., corresponding) casting. For example, the RFID station may read the digital information from the RFID tag of dental impression tray 10 and write the digital information to the RFID tag of the casting, thereby transferring the digital information while the tray and the casting are physically coupled. Alternatively, the RFID station may update the database based on the tag identifiers to logically link the RFID tags without necessarily programming the RFID tags. The RFID station may confirm that a second RFID tag in addition to the casting RFID tag is present within its electromagnetic field and responsive to access prior to updating the database. The construction of the RFID station may include shielding to shape the electromagnetic field to reduce the chances of false access to other RFID tags near the casting station in order to help ensure that the digital information is only transferred or recorded when dental impression tray 10 is physically coupled to the casting.

Manufacturing facility 12 may program the RFID tag of the casting with patient and clinic information from the RFID tag of dental impression tray 10, a date and time at which the casting was performed, information identifying the manufacturing facility and the personnel involved in the casting process, an identifier for the RFID tag within the dental impression tray or other information. In addition, manufacturing facility 12 updates the model record within the database to record the information and updates a status of the model record to "CAST." At this time dental impression tray 10 may be discarded or stored for archival purposes if desired.

The casting then travels to a curing oven, a trimming station and a pedestal bonding (i.e., "mounting") station (80). At each of these stations, manufacturing facility 12 reads the RFID tag of the casting to retrieve and update the model record to reflect the current status of the casting (i.e., "CURED," "TRIMMED" and "MOUNTED"). At each station, manufacturing facility 12 updates the model record in the database, the digital data within the RFID tag of the casting, or both, to include a timestamp and other information.

Next, the casting travels to a scanning station where the casting is scanned and three-dimensional (3D) data is generated that represents a digital model of the patient's dental arch (82). Manufacturing facility 12 utilizes an RFID station at or near the scanning station to update the model record in the database, the digital data within the RFID tag of the casting, or both, to reflect a "SCANNED" status and to include a timestamp and other information associated with the scanning. In some conditions, read-only RFID tags may reduce the likelihood of data loss or corruption that may otherwise result from the scanning process.

Once the model is scanned, personnel within manufacturing facility 12 interact with a 3D modeling workstation to digitally segment the teeth and the gingiva of the digital dental arch into individual, movable virtual components, such as teeth and gingiva (84). Once separated, the 3D data associated with the individual components are imported into the model record of the database (86). As a result, the model record within the database stores digital information captured from the RFID tag of dental impression tray 10 and the RFID tag of the casting for a particular patient as well as the 3D data used to virtually model the dental arch. Manufacturing facility 12 utilizes an RFID station at or near the 3D modeling workstation to update the model record in the database and/or the digital data within the RFID tag to reflect a "SEGMENTED" status and to include a timestamp and other information associated with the segmenting (88).

Manufacturing facility 12 electronically communicates the model record, including the 3D data representing the patient's dental arch, to clinic 8 via network 14 for use in selecting a prescription mid positions for appliances associated with the prescription (90). Orthodontic appliances, such as brackets, buccal tubes, sheaths, etc., may initially be placed in the 3D environment using any of several different methods. For example, brackets may initially be placed in the 3D environment using the method described in copending and commonly assigned U.S. Patent Application Publication No. 05-0130095-A1, Jun. 16, 2005, entitled "Method of Placing Orthodontic Brackets on Teeth in a 3D Virtual World", to Raby, et al., which is incorporated herein by reference in its entirety. Manual adjustment of orthodontic brackets may be assisted by use of visual planar guides, as described in copending and commonly assigned U.S. Patent Application Publication No. 05-0170309-A1, Aug. 4, 2005, entitled "Planar Guides to Visually Aid Orthodontic Appliance Placement within a Three-Dimensional (3D) Environment", to Raby, et al., which is incorporated herein by reference in its entirety. In that application, a system visually aids the user in manual placement of brackets through manual adjustments to bracket position and orientation. Other methods of placing or adjusting the position of brackets on the teeth may also be used. For example, a system for automatic adjustment of an orthodontic appliance to a desired occlusal height is described in copending and commonly assigned U.S. patent application Ser. No. 10/903,686, entitled "Automatic Adjustment of an Orthodontic Bracket to a Desired Occlusal Height Within a Three-Dimensional (3D) Environment", filed Jul. 20, 2004 to Raby, et al., which is incorporated herein by reference in its entirety. It shall be understood that these or any other techniques may be used to initially place the orthodontic appliances on the teeth in the 3D environment. During this process, the model record in the database may be updated to "APPROVED" to indicate a final, approved positioning of the virtual appliances by the practitioner.

Once the practitioner has approved the prescription selection and virtual appliance placement positions, manufacturing facility 12 receives prescription data and appliance location data from clinic 8 via network 14 (92). The prescription data specifies the individual appliances associated with the prescription, and the appliance location data specifies the location of the appliances (e.g., brackets) within the 3D modeling environment.

Next, the casting travels to a robotic placement station within manufacturing facility 12, and appliances are selected and robotically placed on the casting in accordance with the prescription data and the appliance location data (94). An example robotic placement station is described in commonly assigned U.S. Pat. No. 6,123,544, entitled "Method and apparatus for precise bond placement of orthodontic appliances", issued Sep. 26, 2000 to James D. Cleary, hereby incorporated by reference. In one embodiment, as further described below, RFID tags may be fixed to magazines of appliances and used to verify that the types of appliance being placed on the casting match the prescription selected for the patient to which the casting corresponds. Manufacturing facility 12 utilizes an RFID station at or near the robotic placement station to update the model record in the database and the digital data within the RFID tag to reflect a "PHYSICALLY-_PLACED" status and to include a timestamp and other information associated with the placement process.

Next, manufacturing facility 12 utilizes a tray fabricator to produce indirect bonding tray 16 by placing a matrix material over the casting as well as over the brackets placed on the casting (96). For example, manufacturing facility 12 may place a heated plastic sheet matrix material over the casting and the brackets so that plastic sheet material assumes a configuration that precisely matches the casting. At this time, manufacturing facility 12 embeds an RFID tag within the matrix material of indirect bonding tray 16 before the matrix material cools and hardens to form a tray.

Manufacturing facility 12 utilizes an RFID station located at or near the tray fabricator to read the digital information from the RFID tag of casting and optionally program the RFID tag within newly formed indirect bonding tray 16 while the indirect bonding tray is physically coupled to the casting (98). In this manner, manufacturing facility 12 ensures that the digital information is transferred from the casting to the corresponding indirect bonding tray 16. The construction of the RFID station may include shielding to shape the electromagnetic field to reduce the chances of false access to other RFID tags near the tray fabricator in order to help ensure that the digital information is only transferred or otherwise recorded when the casting is physically coupled to indirect bonding tray 16.

Manufacturing facility 12 may update the database and/or transfer data to the RFID tag of indirect bonding tray 16 that includes a patient and clinic information, a unique tag identifier for the RFID tag within the casting, a unique tag identifier for the original dental impression tray 10 associated with the casting and other information stored within the casting. In addition, the RFID station may program a date and time at which the indirect bonding tray was produced, information identifying the manufacturing facility and the personnel involved in the process or other information. Further, manufacturing facility 12 updates the model record within the database to record the information and update a status of the model record to "FABRICATED." At this time the casting may be discarded, shipped to clinic 8, or archived as may be desired.

Finally, manufacturing facility 12 ships indirect bonding tray 16 to clinic 8 individually or in bulk for use in precisely positioning brackets or other appliances on the teeth of patient at precisely the same location specified by the practitioner using the 3D modeling environment (100). When shipping indirect bonding tray 16, the RFID tag within indirect bonding tray 16 may be used to assign and record a shipment date and time within the RFID tag, the database or both. The status within the RFID tag may also be changed to a "SHIPPED" status.

Figure 5:
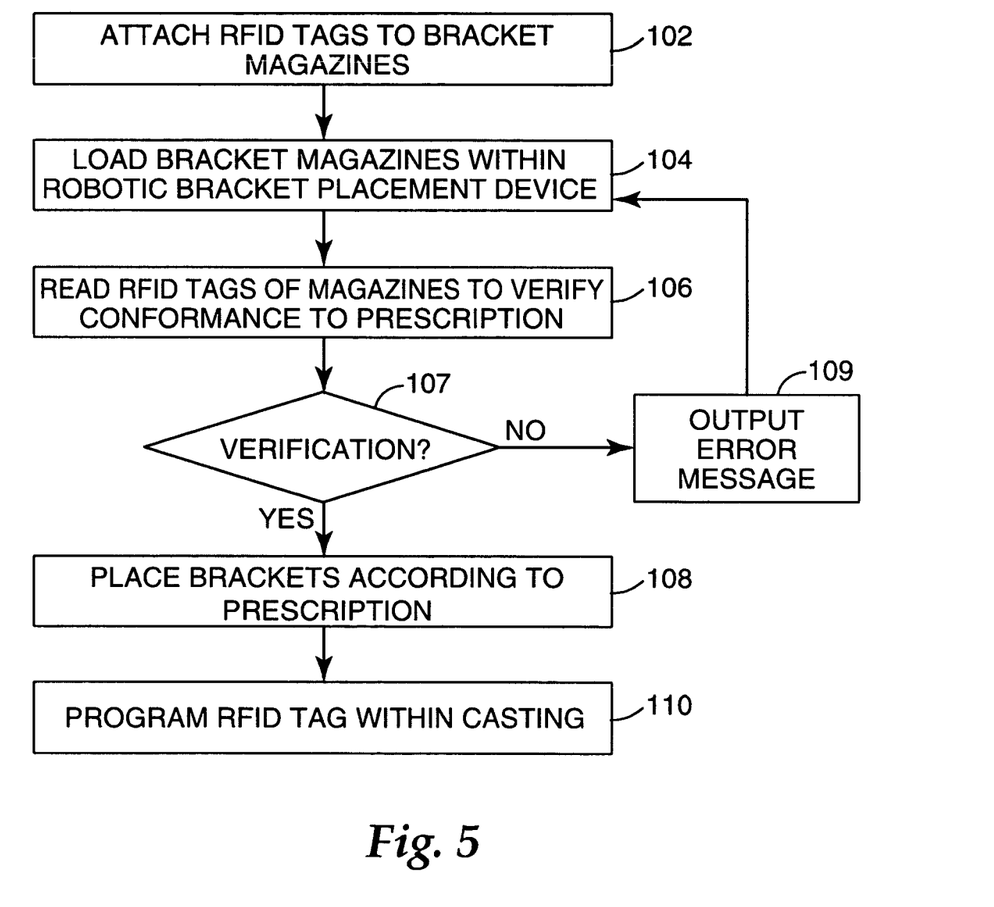
FIG. 5 is a flowchart illustrating in further detail an example process in which RFID tags are utilized during a robotic placement process to ensure that proper appliances are placed on each tooth of a casting.

FIG. 5 is a flowchart illustrating in further detail an example process in which RFID tags are utilized during the robotic placement process to ensure that the proper appliances are placed on each tooth of the casting. Although described with respect to brackets, the techniques may be utilized during the placement of other appliances.

Initially, RFID tags are attached to each bracket holder (also referred to generally as "magazines") within manufacturing facility 12 (102). In one embodiment, the bracket magazines are elongated plastic carriers that carry several brackets of the same type. Each RFID tag is programmed with data identifying the particular type of bracket.

Next, a set of bracket magazines is selected and loaded into a robotic bracket placement device based on a specified prescription (104). In particular, each bracket magazine of the set is inserted into a magazine holder, which is a structure with an array of slots designed to hold all of the magazines corresponding to a single quadrant or full arch of a patient's dentition.

An RFID station at or near the robotic bracket placement device is then used to verify that the correct brackets are being placed on each tooth of the casting (106). In particular, the RFID station first reads the RFID tag embedded within the casting. Based on the identification information in the RFID tag, the RFID station reads the model record from the database to retrieve prescription data and bracket placement data for the specific casting. The RFID station then reads the RFID tags of the magazines loaded into the magazine holders. The RFID station may utilize an antenna and RFID reader located proximate each of the magazine to selectively read the RFID tag associated with each bracket magazine. The RFID station then verifies that the type of bracket specified by the prescription data for each tooth matches the type of bracket loaded into the respective magazine holder of the robotic placement device (107).

If the loaded bracket does not match the prescribed bracket for each tooth, the RFID station outputs an error message (109) and the bracket magazines are reloaded. Otherwise, the robotic bracket placement device is engaged and the brackets are precisely placed on the casting at the locations specified by the practitioner (108). The RFID station at or near the robotic placement station updates the model record in the database and the digital data within the RFID tag to reflect a "PHYSICALLY_PLACED" status and to include a timestamp and other information associated with the placement process (110).

In this manner, the RIFD tags on the magazines are used to ensure that all of the proper brackets are properly staged where the robotic bracket placement device will seek them for placement onto the casting of the patient's teeth.

In one embodiment, each magazine holder includes a discrete antenna and optionally a respective RFID reader set with a low transmit power for very close proximity reading. This may be useful to ensure that only the RFID tag in the magazine proximate a given magazine holder is read and not a neighboring RFID tag. Each magazine may incorporate an electromagnetic shield as a metal layer that lies above the RFID tag. Alternatively, the magazine may be formed entirely out of metal except for a receptacle that holds the tag. The RFID tag may be located on the bottom of the magazine so that RF waves from an antenna in the magazine holder below cannot escape and reach other tags of adjacent magazines. Moreover, in this configuration, one or more magazine holders may be unfilled without causing interference. Even if a magazine holder is unfilled, its respective antenna may still transmit RF waves, but the magazines inserted in the other holders shield their respective tags from the RF waves not emitted by their respective antennas.

In an alternative embodiment, an RFID reader antenna may be located at an end of a mechanical arm of the robot bracket placement device. In this manner, a single reader may be utilized to read RFID tags associated with different magazines as the arm approaches any given magazine.

Figure 6:
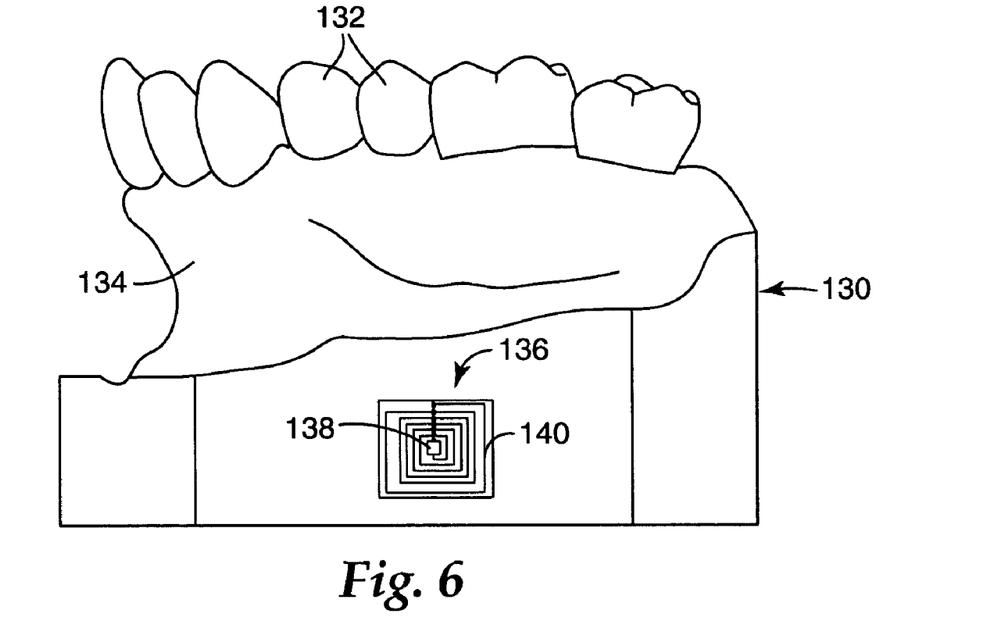
FIG. 6 is a side elevation view of an exemplary casting that provides a replica of a patient's upper dental arch.

FIG. 6 is a side elevation view of an exemplary casting 130 that provides a replica of a patient's upper dental arch. The casting 130 includes a number of replica teeth 132 as well as adjacent portions of replica soft tissue 134 that are similar in shape to the patient's soft tissue or "gums." Casting 130 may include replicas of all of the teeth in the patient's upper (or lower) arch. If the impression is accurately taken and the casting 130 is carefully prepared, the replica teeth 132 and replica soft tissue 134 will have a configuration and orientation that are identical to the configuration and orientation of the corresponding teeth and soft tissue of the orthodontic patient.

As shown in FIG. 6, casting 130 includes an RFID tag 136 that was embedded during the casting process. RFID tag 136 includes an integrated circuit 138 and an antenna 140 that receives RF energy from a source, and backscatters RF energy in a manner well known in the art. It is this backscattered RF energy that provides a signal by which an interrogator, such as an RFID reader or detection system, obtains information from RFID tag 136 and, more particularly, about casting 130 within which RFID tag 136 is embedded or affixed. It shall be understood by those skilled in the art that any appropriate form or configuration of antenna may be used, and the invention is not limited to the particular form of antenna 140 depicted in FIG. 6.

Figure 7:
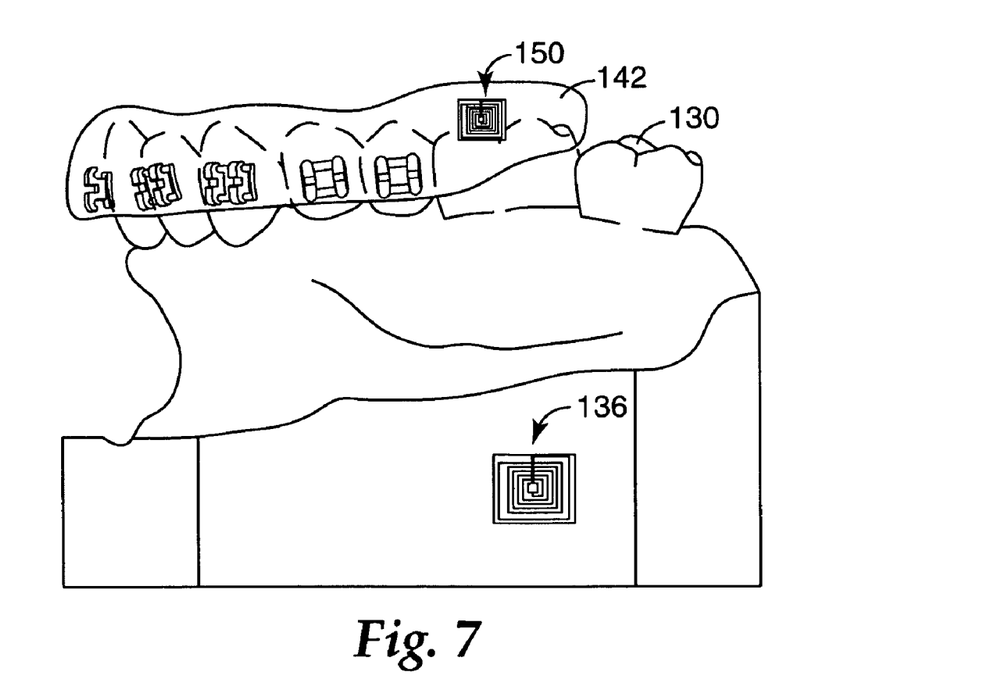
FIG. 7 is a side elevation view of the casting of FIG. 6 except that appliances have placed on the casting and a quantity of matrix material has been placed over the casting in order to make an indirect bonding tray.

FIG. 7 is a side elevation view of casting 130 similar to FIG. 6 except that appliances 144 have been placed on the casting and a quantity of matrix material has been placed over the casting and the appliances in order to form an indirect bonding tray 142. As illustrated in FIG. 7, an RFID tag 150 has been embedded within or otherwise affixed to indirect bonding tray 142 while the matrix material is sufficiently soft. As described herein, an RFID station (not shown in FIG. 7) may read digital information from RFID tag 136 of casting 130 and transfer the digital data to RFID tag 150 of indirect bonding tray 142 while the casting and the indirect bonding tray are physically coupled.

Various implementations and embodiments of the invention have been described. Nevertheless, it is understood that various modifications can be made without departing from the invention. These and other embodiments are within the scope of the following claims.

The invention claimed is:

1. A method comprising:
    forming a casting from a dental impression tray having an impression of a tooth structure of a patient, wherein the dental impression tray includes a radio-frequency identification (RFID) tag;
    associating an RFID tag with the casting;
    reading digital information from the RFID tag of the dental impression tray;
    programming the RFID tag associated with the casting with at least a portion of the digital information from the RFID tag of the dental impression tray while the casting is physically coupled to the dental impression tray; and
    storing digital information that associates the RFID tag of the casting with the RFID tag of the dental impression tray.

2. The method of claim 1, wherein reading the digital information comprises reading patient-specific digital information or a unique tag identifier from the RFID tag of the dental impression tray.

3. The method of claim 1, wherein programming the RFID tag associated with the casting comprises writing at least one of:
   a patient identifier uniquely identifying the patient,
   a model identifier uniquely identifying the casting from other physical models associated with the patient;
   a clinic identifier identifying a clinic at which the impression of the tooth structure was made,
   a tag identifier for the RFID tag associated with the dental impression tray,
   a date and time at which the impression of the tooth structure was captured,
   an identifier identifying a manufacturing facility where the dental impression tray was produced, and
   information identifying any personnel involved in the forming of the impression.

4. The method of claim 1, wherein storing the digital information comprises storing at least one of:
   a patient identifier uniquely identifying the patient,
   a clinic identifier identifying a clinic at which the impression of the tooth structure was made,
   a tag identifier for the RFID tag associated with the dental impression tray,
   a date and time at which the impression of the tooth structure was captured,
   an identifier identifying a manufacturing facility where the dental impression tray was produced, and
   information identifying any personnel involved in the forming of the impression.

5. The method of claim 1, wherein storing digital information comprises updating a database to include a model record that associates the RFID tag of the casting with the RFID tag of dental impression tray.

6. The method of claim 5, wherein updating the model record comprises:
   reading first digital information from the RFID tag of the dental impression tray;
   reading second digital information from the RFID tag of the casting; and
   updating the model record to include the first and second digital information.

7. The method of claim 6,
   wherein the first digital information includes patient-specific digital information or a unique tag identifier read from the RFID tag of the dental impression tray, and
   wherein the second digital information includes a unique tag identifier read from the RFID tag of the casting.

8. The method of claim 1, wherein associating an RFID tag with the casting comprises at least partially embedding the RFID tag within the casting while forming the casting.

9. The method of claim 1,
   wherein reading digital information comprises reading a patient identifier from the RFID tag of the dental impression tray with an RFID reader, and
   wherein storing digital information comprises writing the patient identifier to the RFID tag of the casting while the casting is physically coupled to the dental impression tray.

10. The method of claim 1, further comprising:
    forming an indirect bonding tray from the casting;
    associating an RFID tag with the indirect bonding tray;
    reading digital information from the RFID tag of the casting;
    programming the RFID tag associated with the indirect bonding tray with the digital information from the RFID tag of the casting while the indirect bonding tray is physically coupled to the casting; and
    storing digital information that associates the RFID tag of the indirect bonding tray with the RFID tag of the casting.

11. The method of claim 10, wherein the digital information read from the RFID tag of the casting comprises patient-specific digital information or a unique tag identifier for the RFID tag of the casting.

12. The method of claim 10, wherein storing digital information comprises updating a database to include a model record that associates the RFID tag of the casting with the RFID tag of indirect bonding tray.

13. The method of claim 10,
    wherein forming an indirect bonding tray comprises placing one or more orthodontic appliances on the casting and flowing a quantity of matrix material over the casting, and
    wherein associating an RFID tag with the indirect bonding tray comprises at least partially embedding the RFID tag within the matrix material.

14. The method of claim 13, wherein the orthodontic appliances comprise brackets, buccal tubes or sheaths.

15. The method of claim 10, wherein programming the RFID tag associated with the indirect bonding tray comprises writing at least one of:
    a patient identifier uniquely identifying the patient,
    a model identifier uniquely identifying the casting from other physical models associated with the patient;
    a clinic identifier identifying a clinic at which the impression of the tooth structure was made,
    a tag identifier for the RFID tag associated with the casting,
    a tag identifier for the RFID tag associated with the dental impression tray,
    a date and time at which the indirect bonding tray was produced,
    an identifier identifying a manufacturing facility where the indirect bonding tray was produced,
    information describing at least one orthodontic appliance coupled to the indirect bonding tray; and
    information identifying any personnel involved in the production of the indirect bonding tray.

16. The method of claim 10, wherein forming an indirect bonding tray comprises:
    inserting at least one appliance magazine within a robotic placement device, wherein the appliance magazine includes an RFID tag having digital information identifying a type of orthodontic appliance loaded within the appliance magazine; and
    accessing the RFID tag of the appliance magazine and the RFID tag of the casting to verify that the type of orthodontic appliance inserted within the robotic placement device matches a prescription for the patient.

17. The method of claim 16, further comprising:
    reading the digital information from the RFID tag of the casting;
    accessing a database to determine a prescription comprising a set of one or more orthodontic appliances based on the digital information;
    reading the digital information from the RFID tag of the appliance magazine to identify the type of orthodontic appliance loaded within the magazine; and comparing the set of orthodontic appliances of the prescription with the type of appliance loaded within the magazine.

18. The method of claim 16, wherein the tooth structure comprises a plurality of teeth, the method further comprising verifying that the type of orthodontic appliance inserted within the robotic placement device matches a prescription for the patient for each of the teeth.

19. The method of claim 1, further comprising:
scanning the casting to generate digital data that provides a three-dimensional (3D) representation of the tooth structure; and
updating a database to include a model record that associates a unique identifier for the RFID tag of the casting with the digital data.

20. The method of claim 19, further comprising:
communicating the digital data to a clinic via a computer network;
receiving prescription data and appliance location data from the clinic via the network; and
updating the database to associate the prescription data and the appliance location data with the model record.

21. The method of claim 1, further comprising:
scanning the dental impression tray to generate digital data that provides a three-dimensional (3D) representation of the tooth structure; and
updating a database to include a model record that associates a unique identifier for the RFID tag of the dental impression tray with the digital data.

* * * * *

UNITED STATES PATENT AND TRADEMARK OFFICE
CERTIFICATE OF CORRECTION

PATENT NO. : 7,473,097 B2
APPLICATION NO. : 11/015368
DATED : January 6, 2009
INVENTOR(S) : Richard E. Raby It is certified that error appears in the above-identified patent and that said Letters Patent is hereby corrected as shown below:

Column 2
Line 44-45, Delete "5,429,299" and insert -- 5,429,229. --, therefore.

Column 7
Line 29, Delete "stare" and insert -- store --, therefore.
Line 62, Delete "fray" and insert -- tray --, therefore.
Line 64, Delete "interroagates" and insert -- interrogates --, therefore.

Column 8
Line 2, Delete "fray" and insert -- tray --, therefore.
Line 5, Delete "pro-applied" and insert -- pre-applied --, therefore.
Line 5, After "to" insert -- the --.

Column 10
Line 62, Delete "incoporated" and insert -- incorporated --, therefore.

Column 13
Line 39, Delete "mid" and insert -- and --, therefore.

Signed and Sealed this

Twenty-fourth Day of March, 2009

JOHN DOLL
*Acting Director of the United States Patent and Trademark Office*